(12) United States Patent
Nam et al.

(10) Patent No.: US 6,968,038 B2
(45) Date of Patent: Nov. 22, 2005

(54) APPARATUS AND METHOD FOR GENERATING HIGH-ORDER HARMONIC X-RAY, AND POINT-DIFFRACTION INTERFEROMETER USING HIGH-ORDER HARMONIC X-RAY

(75) Inventors: Chang Hee Nam, Daejeon (KR); Dong Gun Lee, Pusan (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 67 days.

(21) Appl. No.: 10/626,748

(22) Filed: Jul. 22, 2003

(65) Prior Publication Data

US 2004/0174955 A1 Sep. 9, 2004

(30) Foreign Application Priority Data

Mar. 6, 2003 (KR) ...................... 10-2003-0014134

(51) Int. Cl.$^7$ ............................................. H01J 35/32
(52) U.S. Cl. ................................................... 378/122
(58) Field of Search ........................ 378/119, 143, 122; 372/5

(56) References Cited

U.S. PATENT DOCUMENTS

| | | | |
|---|---|---|---|
| 3,961,197 A | 6/1976 | Dawson ...................... | 378/119 |
| 5,835,217 A | 11/1998 | Medecki ...................... | 356/521 |
| 6,349,128 B1 | 2/2002 | Nelson ........................ | 378/44 |
| 6,706,154 B1 | 3/2004 | Yang et al. ............. | 204/157.15 |

OTHER PUBLICATIONS

Miyazaki, K. et al. High Order Harmonic Generation in the Soft X-Ray to XUV by Ultra short Laser Pulses; Lasers & Electro-Optics Society Annual Meeting—Conference Proceedings Nov. 15-18, 1993; pp. 758-759.

Chang, Zenghu Generation of Coherent, Femtosecond, X-ray Pulses in the "Water Window;" IEEE Journal of Selected Topics in Quantum Mechanics, vol. 4, Issue 2, Mar.-Apr. 1998; pp 266-270.

Nam, Chang Hee et al. Tunable Coherent Femtosecond Soft X-ray Source Based on High-Harmonic Generation; Lasers & Electro Optics; The Pacific Rim Conference vol. 1, Aug. 30-Sep. 3, 1999; pp. 74-75.

Bartels, R et al. Control of High-Order Harmonic Generation Through Shaped Pulse Optimization; Nonlinear Optics: Materials, Fundamentals and Applications—Technical Digest, Aug. 6-10, 2000; pp. 289-291.

*Primary Examiner*—David V. Bruce
*Assistant Examiner*—Courtney Thomas
(74) *Attorney, Agent, or Firm*—Bachman & LaPointe, P.C.

(57) ABSTRACT

Disclosed herein is a point-diffraction interferometer which can inspect a surface quality of an optical system for extreme ultraviolet lithography using a high-order harmonic X-ray source with excellent coherence, and an apparatus and method for generating a high-order harmonic X-ray. The present invention uses a high-order harmonic X-ray beam as a coherence light source, thus remarkably reducing the size of an apparatus for generating a light source to approximately $\frac{1}{100}$ of a device using a light source generated in a conventional synchrotron. Further, the present invention simplifies the construction of an interferometer by employing a thin foil in which a pinhole is formed through a drilling technique using high power femtosecond laser, thus increasing the industrial utility of the interferometer.

7 Claims, 6 Drawing Sheets

--Fig. 1--
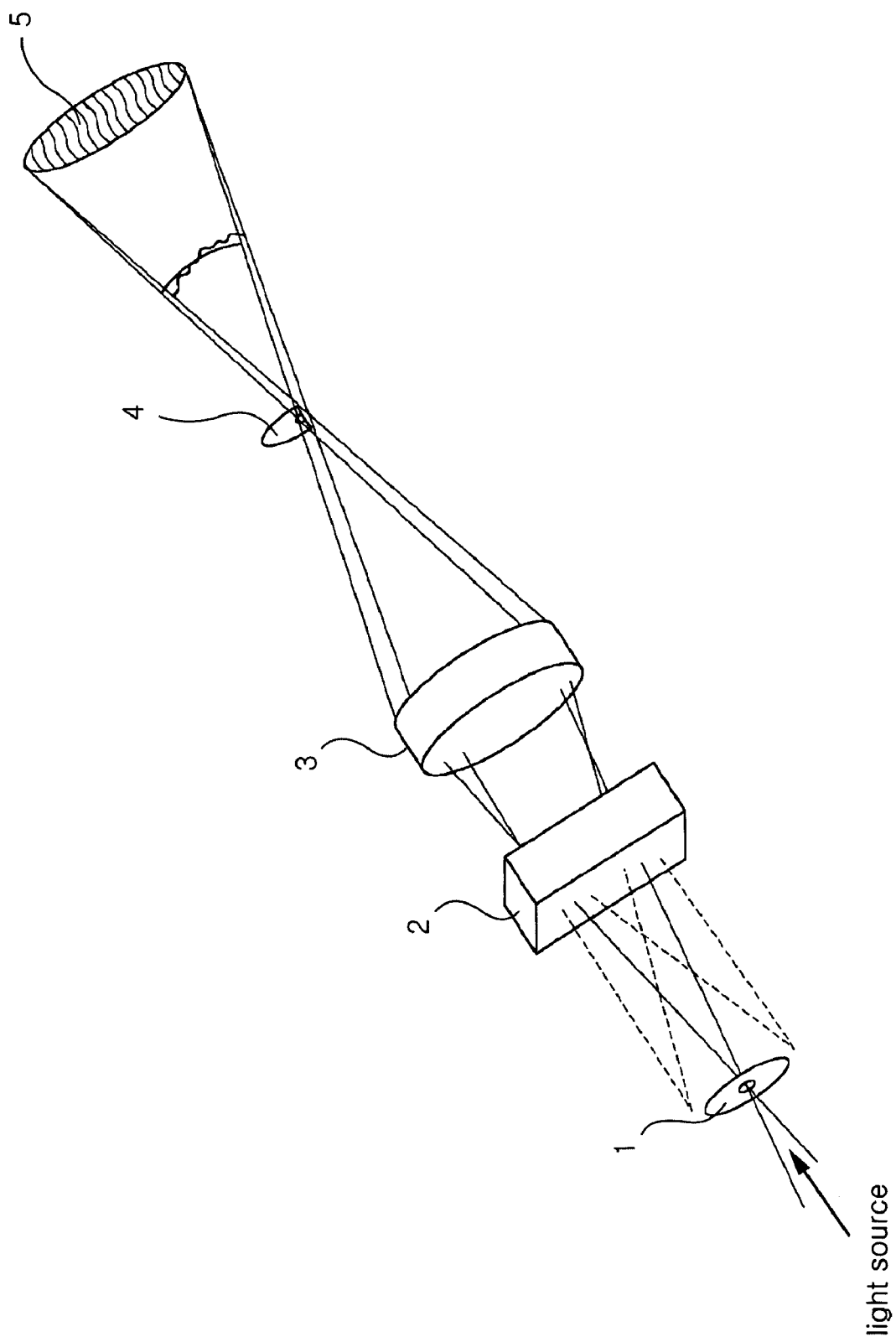

--Fig. 2--
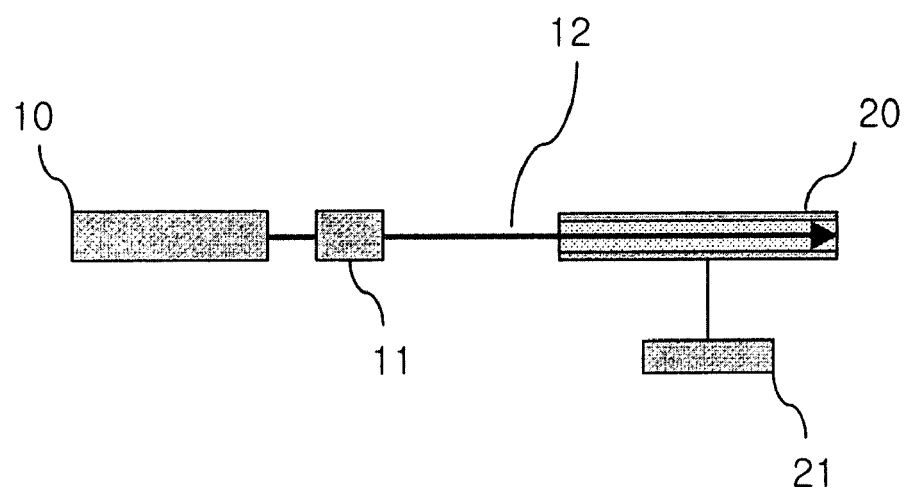
--Fig. 3--
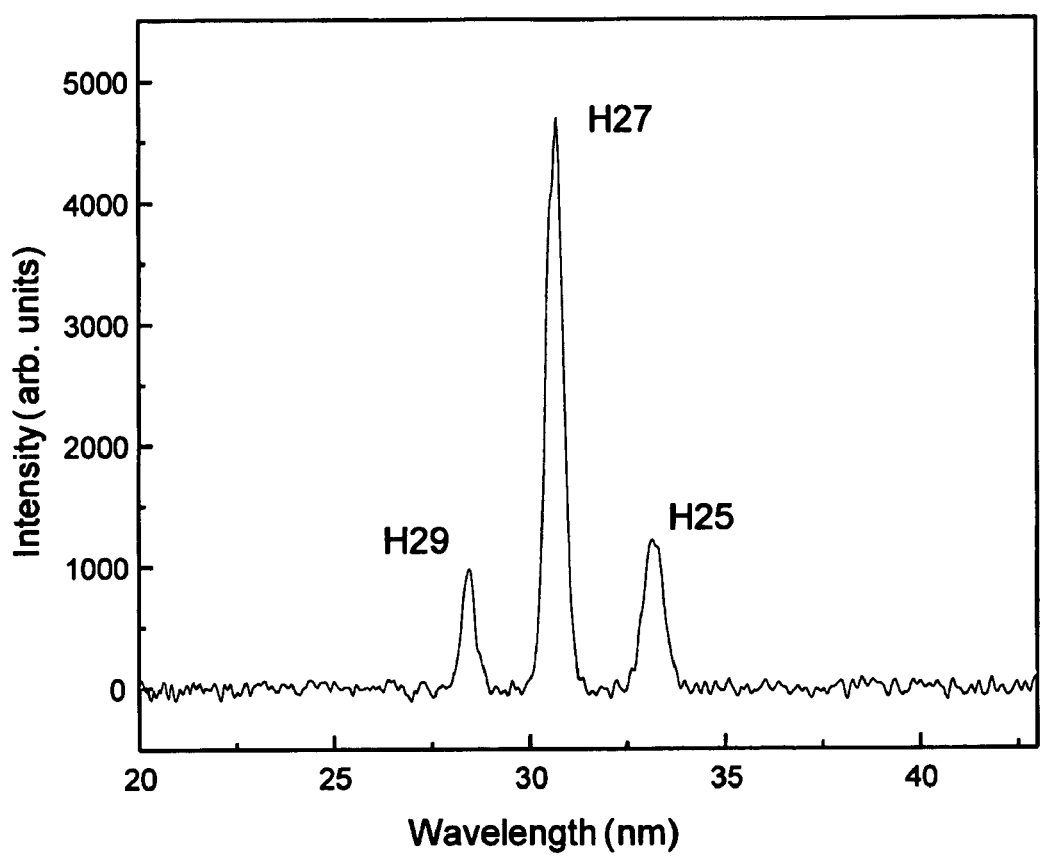

--Fig. 4--
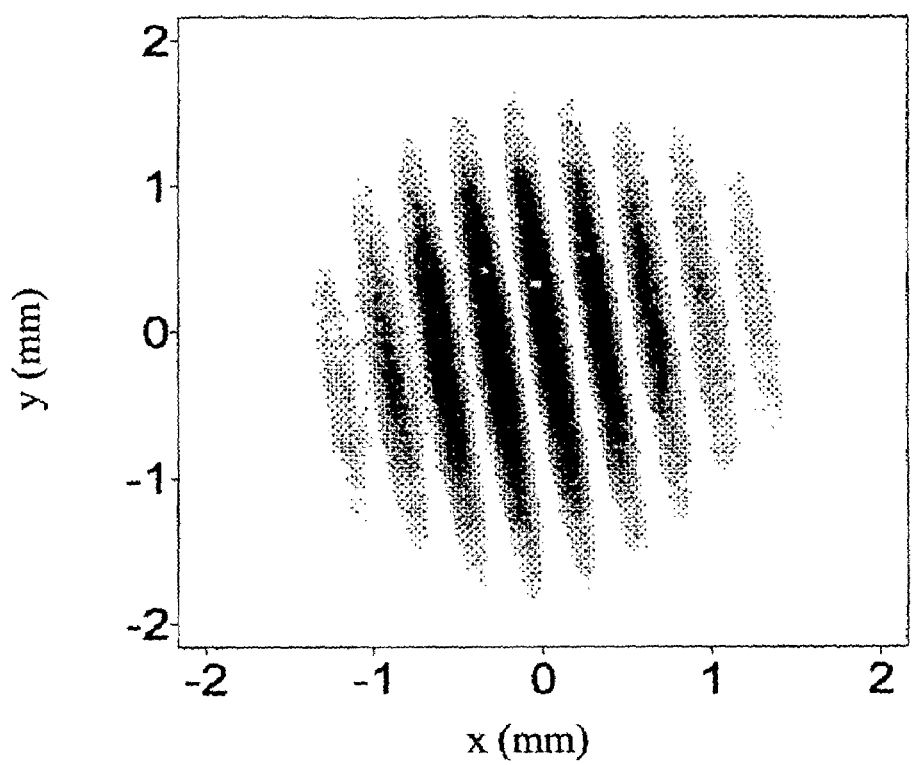
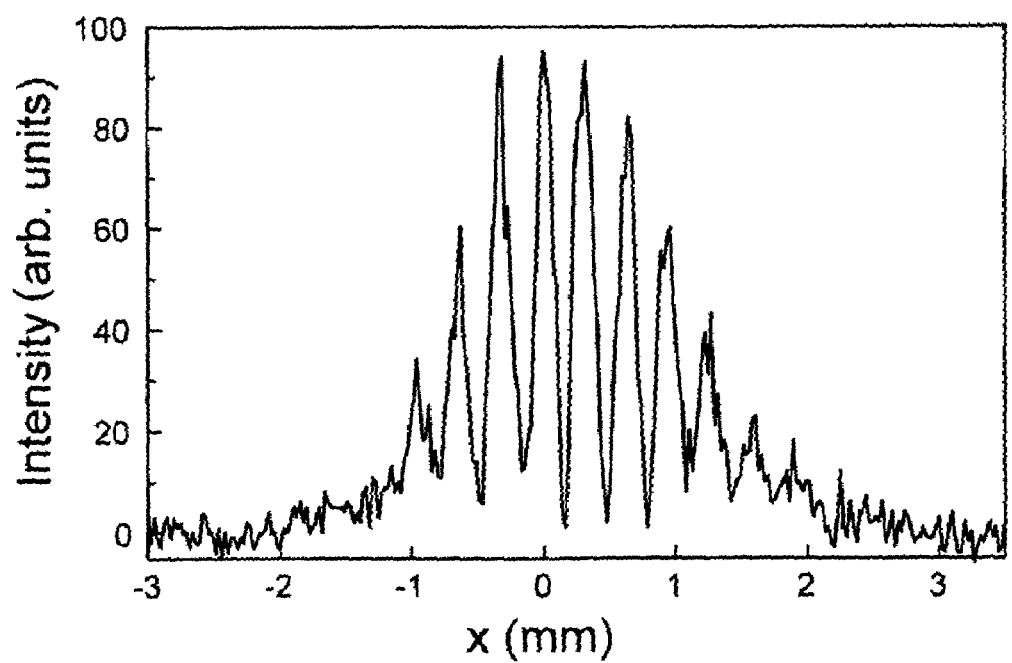

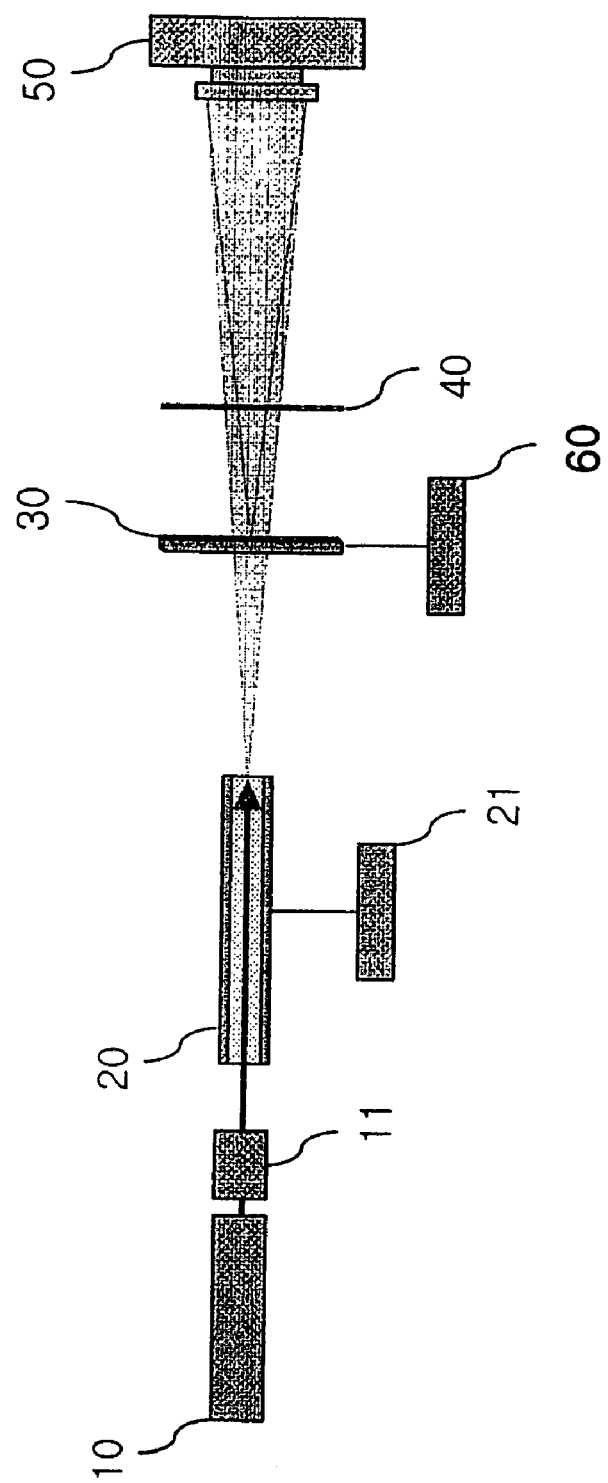
--Fig. 5--

--Fig. 6--
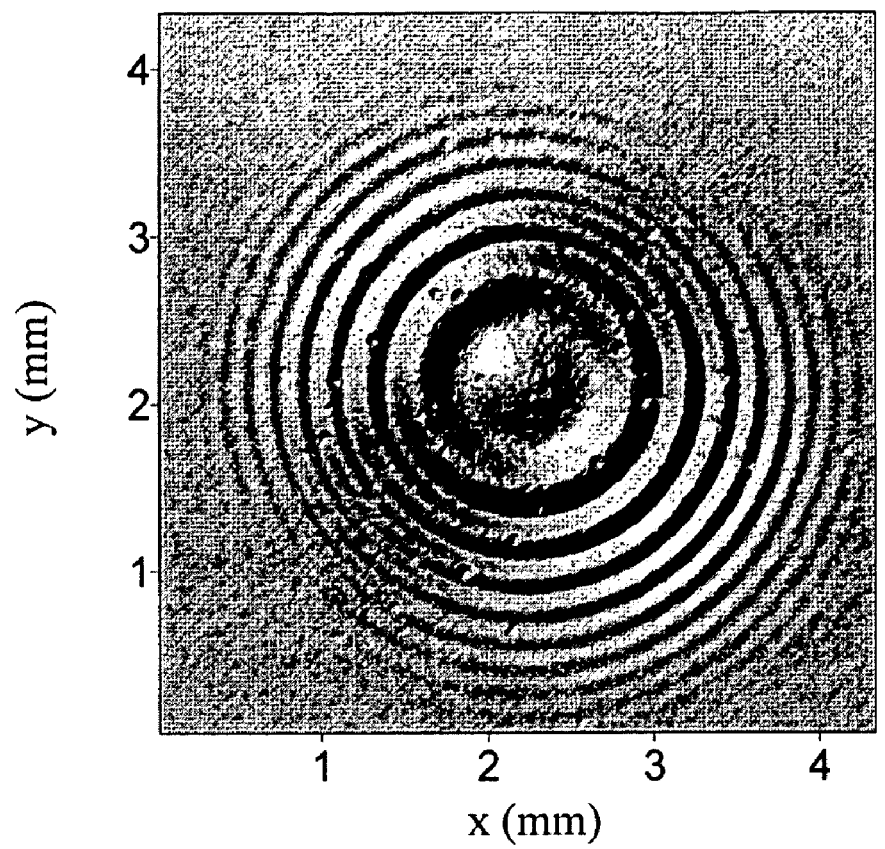
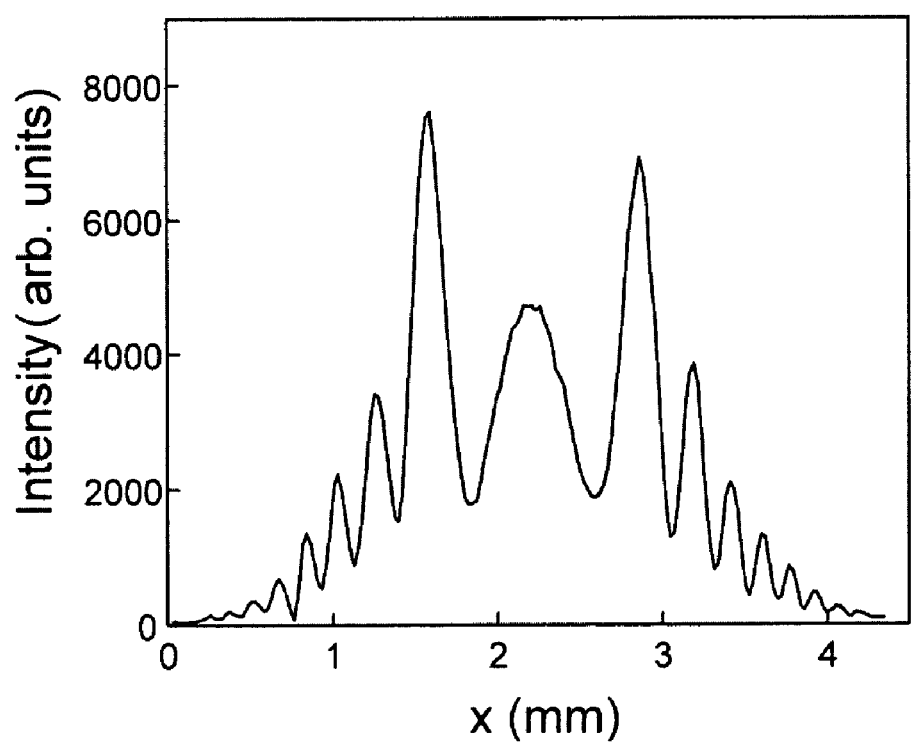

--Fig. 7--
Wave-front radius (R = 1.19 m)
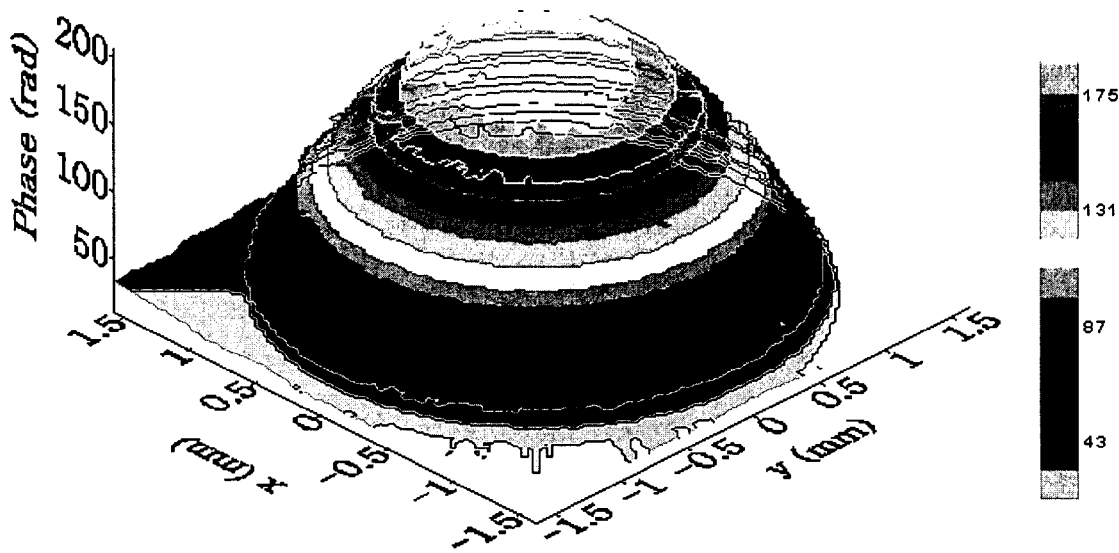
--Fig. 8--
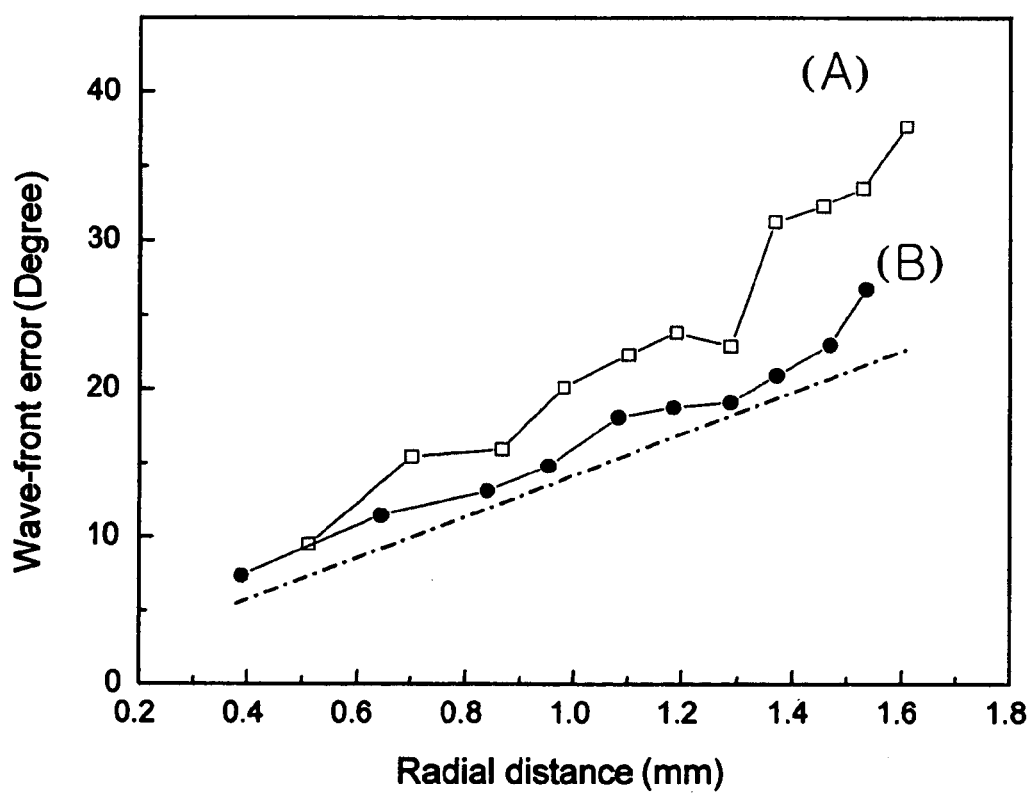

US 6,968,038 B2

APPARATUS AND METHOD FOR GENERATING HIGH-ORDER HARMONIC X-RAY, AND POINT-DIFFRACTION INTERFEROMETER USING HIGH-ORDER HARMONIC X-RAY

BACKGROUND OF THE INVENTION

1. Field of the Invention

The present invention relates generally to an apparatus and method for generating a high-order harmonic X-ray, and a point-diffraction interferometer using the high-order harmonic X-ray, and more particularly to an apparatus and method for generating a high-order harmonic X-ray source with excellent coherence and realizing a point-diffraction interferometer which can inspect a surface quality of an optical system for extreme ultraviolet lithography using the high-order harmonic X-ray source.

2. Description of the Prior Art

Generally, an interferometer is a device for dividing light emitted from a single light source into two or more light beams in an appropriate manner, overlapping divided light beams to cause the light beams to interfere with one another, and observing an interference pattern of the interfered light beams. An interferometer was mainly used to measure wavelengths, precisely compare lengths or distances, compare optical distances, and perform other functions. In recent years, the utilization range of the interferometer has been widened to applications for inspecting a surface quality of an optical system or the like.

There are a "point-diffraction interferometer using an X-ray generated in a synchrotron", a "point-diffraction interferometer using a white light" or the like as the interferometer used for the above purpose.

The point-diffraction interferometer using an X-ray generated in a synchrotron employs an X-ray generated in the synchrotron as a light source, so the point-diffraction interferometer must use a synchrotron so as to generate the light source. However, such point-diffraction interferometer is problematic in that the access to a huge synchrotron (with the size of several hundreds of meters) is limited and it is difficult to inspect a great number of optical systems for industrial use.

Meanwhile, in an interferometer used for inspection or measurement, a light source must be coherent. However, the above point-diffraction interferometer using an X-ray generated in synchrotron is problematic in that additional devices are required to improve the coherence of the light source, thus complicating the entire construction and operation of a measuring device and greatly weakening the intensity of light reaching a sample from a light source.

Meanwhile, a point-diffraction interferometer, in which a pinhole 1 for improving coherence is disposed between a light source and a radiation optical system 3, and a beam splitter 2 for dividing a beam into two separate beams is disposed between the pinhole 1 and the radiation optical system 3, is disclosed in U.S. Pat. No. 5,835,217 by Medecki, et al., entitled a "Phase-shifting point-diffraction interferometer", as shown in FIG. 1.

This apparatus is advantageous in that it uses a white light passing through the pinhole 1, so a short coherence length of the white light is sufficiently utilized to obtain a good interference pattern 5, while it is disadvantageous in that it requires the pinhole 1 which is an additional device for improving the coherence of a light source as described above. A similar circumstance holds for the case of a point diffraction interferometer that uses X-ray from a synchrotron.

SUMMARY OF THE INVENTION

Accordingly, the present invention has been made keeping in mind the above problems occurring in the prior art, and an object of the present invention is to provide an apparatus and method for generating a high-order harmonic X-ray, which is a coherent X-ray source, without requiring an additional device to improve coherence.

Another object of the present invention is to provide a point-diffraction interferometer, which can be greatly simplified in construction and inspect a surface quality of an optical system for extreme ultraviolet lithography using a high-order harmonic X-ray source having excellent coherence and a high power femtosecond laser drilling technique for enabling a micro hole to be formed in a thin foil.

In order to accomplish the above object, the present invention provides a high-order harmonic X-ray generating apparatus for generating a coherent high-order harmonic X-ray beam, comprising a high power femtosecond laser; a laser intensity controller for adjusting laser intensity and beam size of a femtosecond laser pulse generated by the high power femtosecond laser; a gas- filled hollow tube target for generating a high-order harmonic X-ray beam; and a gas pressure controller for adjusting the pressure of the target gas.

Further, the present invention provides a point-diffraction interferometer using a high-order harmonic X-ray, comprising an interferometer plate implemented by a thin foil having a pinhole and arranged to be perpendicular to an incident path of a high-order harmonic X-ray beam for generating a diffracted beam through the pinhole forming a reference beam and a transmitted beam; and an X-ray detector disposed on the path of the reference and transmitted beams to detect an interference pattern generated through the interference of the reference and transmitted beams.

Further, the present invention provides a high-order harmonic X-ray generating method, the method generating a coherent high-order harmonic X-ray by focusing a high power femtosecond laser beam into a gas-filled hollow tube target, comprising the steps of controlling pressure of the gas and reducing the intensity of long-wavelength harmonics with orders less than a predetermined order using an X-ray filter with low transmissivity in a long wavelength region; reducing the intensity of short-wavelength harmonics with orders greater than the predetermined order by adjusting focused intensity of the high power femtosecond laser beam; and allowing harmonics near the predetermined order to be phase-matched by adjusting the beam size of the high power femtosecond laser.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a view showing the construction of a conventional point-diffraction interferometer;

FIG. 2 is a view showing the construction of an apparatus for generating a high-order harmonic X-ray according to the present invention;

FIG. 3 is a view showing an extreme ultraviolet spectrum of high-order harmonics generated by a high power femtosecond laser pulse;

FIG. 4 is a view showing results of an interference experiment for double pinholes using a high-order harmonic X-ray;

FIG. 5 is a view showing the construction of a point-diffraction interferometer according to the present invention;

FIG. 6 is a view-showing point-diffraction interferogram using a high-order harmonic X-ray beam;

FIG. 7 is a view showing a wave-front phase of a high-order harmonic X-ray beam reconstructed using an interference pattern; and FIG. 8 is a graph showing a wave-front phase measurement error and the wave-front phase error of the high-order harmonic X-ray beam.

DESCRIPTION OF THE PREFERRED EMBODIMENTS

Hereinafter, embodiments of the present invention will be described in detail with reference to the attached drawings.

FIG. 2 is a view showing the construction of an apparatus for generating a coherent high-order harmonic X-ray according to the present invention. As shown in FIG. 2, the coherent high-order harmonic X-ray generating apparatus of the present invention comprises a high power femtosecond laser 10, a laser intensity controller 11, a gas-filled hollow tube target 20, and a gas pressure controller 21.

In the present invention, a laser pulse 12 generated by the high power femtosecond laser 10 is focused into the gas-filled hollow tube target 20 so as to generate a high-order harmonic X-ray which is a coherent X-ray source. In this way, if the laser pulse is focused into the gas, electrons of target atoms are ionized by the femtosecond laser pulses, and high-order harmonics are emitted during the recombination of the ionized electrons. High-order harmonics are normally generated at odd orders of the pumping laser wavelength, so the spectral width of the generated high-order harmonics is very wide.

Therefore, in the present invention, the range of generated harmonics is controlled to 29-th from 25-th, peaking at 27-th harmonic, so as to enhance the coherence length of an X-ray beam, thus generating coherent X-ray beams having a spectral width equal to or less than 4 nm.

In this case, a method of selecting the range of the generated wavelengths of high-order harmonics is described below. First, the intensity of harmonics with wavelengths longer than that of 27-th harmonic is rapidly reduced by appropriately adjusting the pressure of gas (due to the absorption by neutral gas) through the gas pressure controller 21, and employing an X-ray filter with very low transmissivity in a long wavelength region. Next, the focused intensity of a laser beam is appropriately adjusted through the laser intensity controller 11 to set the highest generated harmonic order to be equal to or less than 29-th, thus eliminating harmonics with wavelengths shorter than that of the 29-th harmonic. Finally, the focusing conditions of the laser beam (adjustment of the size of an incident laser beam in the present invention) are set to conditions in which harmonics near the 27-th harmonic are phase-matched, thus enabling the energy of the 27-th harmonic to be a significant portion of total generated harmonic energy.

For example, in the present invention, provided that a width of each laser pulse is 20 femtoseconds, energy per laser pulse is 0.35 mJ, and argon gas is filled into a hollow glass tube target with a length of 4 cm and a core diameter of 350 $\mu$m, it can be proved that the 27-th harmonic contains more than 68% of totally generated harmonic energy.

FIG. 3 is a view showing an extreme ultraviolet spectrum of high-order harmonics generated by high power femtosecond laser pulses as described above. As a single harmonic order is dominantly generated in this manner, making the spectral width of entire harmonics narrow, the high-order harmonic X-ray generation apparatus is advantageous in that it can be directly applied to an X-ray interferometer without employing an additional device to obtain monochromatic light, used in the prior art.

FIG. 4 is a view showing results obtained by measuring the coherence of high-order harmonics generated in the present invention. In the present invention, a double pinhole interferometer is constructed to measure the coherence of high-order harmonics, as shown in FIG. 5. As a result, since an interferogram represents clear contrast between its maximum and minimum values in FIG. 4 (giving the visibility of "1"), it is seen that the spatial coherence of a high-order harmonic X-ray beam is excellent. Since the excellent spatial coherence of the high-order harmonic X-ray beam according to the present invention yields the high visibility of the interferogram as shown in FIG. 4, the high-order harmonic X-ray apparatus is advantageous to accurately quantify the interference pattern. Further, it can be proved that this coherent X-ray source is directly used in the X-ray interferometer without requiring additional processing of harmonic X-rays. Therefore, the present invention does not require an additional device for improving coherence due to the excellent spatial coherence of the high-order harmonic beams, clearly differing from a device using an X-ray source generated in a synchrotron as one of conventional devices.

Hereinafter, the construction of the point-diffraction interferometer using a coherent high-order harmonic X-ray is described. The point-diffraction interferometer according to the present invention basically comprises a point-diffraction interferometer plate 30 for receiving a high-order harmonic X-ray beam and generating diffracted reference beam and transmitted incident beam, and an X-ray detector 50 for detecting an interference pattern.

FIG. 5 illustrates a point-diffraction interferometer according to an embodiment of the present invention, and shows an embodiment in which a high-order harmonic X-ray beam generated by the high-order harmonic X-ray generating apparatus, consisted of a high power femtosecond laser generator 10 and a target 20 for generating the high-order harmonic X-ray beam as described above, is used. However, those skilled in the field would appreciate that the present invention can be implemented in such a way that another apparatus for generating a high-order harmonic X-ray beam using another method, besides the coherent high-order harmonic X-ray generating apparatus and method proposed in the present invention, is alternatively provided.

The embodiment of FIG. 5 comprises a high power femtosecond laser 10, a target 20 for generating a high-order harmonic X-ray beam, a point-diffraction interferometer plate 30 for dividing the beam into two beams, a thin X-ray filter 40 with appropriate thickness, and an X-ray detector 50 for detecting an interference pattern.

In this case, the point-diffraction interferometer plate 30 for generating a transmitted beam and a reference beam is manufactured in such a way that a pinhole is formed in a thin foil using a high power femtosecond laser drilling technique. Specifications of the point-diffraction interferometer plate 30 and the aluminum filter 40 greatly influence the optimization of the visibility of an interference pattern to be observed. In the present invention, the specifications are determined after the wave-front propagation of X-ray beam has been previously ascertained through simulations. Further, in the present invention, the point-diffraction interferometer plate 30 is implemented so that X and Y coordinates thereof can be freely adjusted by actuators, thus enabling a relative position between a harmonic beam and a pinhole to be easily adjusted.

Meanwhile, the aluminum filter 40, which is an X-ray filter and serves to eliminate noise components originating from the laser beam, can be disposed between the point-diffraction interferometer plate 30 and the X-ray detector 50.

FIG. 6 is a view showing a diffraction interferogram and visibility thereof, measured under the conditions, in which the thickness of the interferometer plate made of aluminum is 1 $\mu$m and the diameter of a pinhole in the interferometer plate is 10 $\mu$m, and obtained using the high-order harmonic X-ray beam of the present invention. As shown in FIG. 6, the visibility determined by the difference between a maximum value of an interference fringe pattern and a minimum value of an adjacent interference fringe pattern is greater than 50% for almost entire region of the interferogram.

FIG. 7 is a view showing results obtained by reconstructing a wave-front phase of a high-order harmonic X-ray beam using the information of this interference pattern. It can be seen in FIG. 7 that the shape of the reconstructed wavefront is close to that of a spherical wave, and a radius of the wave-front phase in this case is 1.19 m. Once a wavefront phase is known, the intensity distribution of a beam depending on the propagation of the high-order harmonic X-ray beam can be determined. For example, how the intensity distribution of a harmonic beam changes after the harmonic beam passes through a certain X-ray optical system can be predicted. The harmonic wave-front phase information indicated in FIG. 7 provides beam propagation information necessary for the design of an optical system using an X-ray beam.

FIG. 8 is a graph showing a phase error between a wave-front phase reconstructed according to focusing conditions of a laser beam to generate a high-order harmonic X-ray beam, and a wave-front phase of a spherical wave. In FIG. 8, (A) shows results measured in the case where a wave-front phase of a generated high-order harmonic X-ray beam is quite different from that of a spherical wave. In this case, (A) shows that the phase error can be measured with sufficient accuracy using the high-order harmonic point-diffraction interferometer of the present invention. Further, (B) shows results measured in the case where the focusing condition of the laser beam is varied to allow the wave-front phase of the generated high-order harmonic X-ray beam to be similar to that of the spherical wave. In this case, (B) shows that the phase error is less than $\lambda/15$ over an entire region of the X-ray beam. A high-order harmonic beam itself, generated to be close to a spherical wave with a very small error, can be a reference spherical wave. Therefore, the surface quality of an extreme ultraviolet optical system can be recognized by measuring how the wave-front phase of a beam passing through the extreme ultraviolet optical system deviates from that of the spherical wave. This shows that a high-order harmonic X-ray beam can be directly used to measure the surface quality of the extreme ultraviolet optical system without requiring additional processing or device.

As described above, the present invention provides a high-order harmonic X-ray generating apparatus and method, which can generate a high-order harmonic X-ray beam, which is a coherent X-ray source, by focusing a high power femtosecond laser pulse into a gas-filled target and maintaining suitable conditions, and can remarkably reduce the size of the apparatus for generating a coherent X-ray light source, compared to a conventional synchrotron X-ray source, by utilizing the high-order harmonic X-ray beam, thus simplifying the construction of the apparatus compared to the conventional device, and consequently improving the industrial utility thereof. This is because the apparatus can be implemented without using additional devices for improving the coherence of a light source required when an X-ray beam emitted from a conventional synchrotron X-ray source is used.

Further, the present invention is advantageous in that the performance of a point-diffraction interferometer using the high-order harmonic X-ray beam as a light source is also excellent due to the excellent coherence of the high-order harmonic X-ray beam.

Further, the present invention is advantageous in that it has utilities applicable to actual industrial fields due to the small-sized apparatus and the excellent performance as described above, and it can inspect the surface quality of an extreme ultraviolet optical system using the high-order harmonic X-ray point-diffraction interferometer of the present invention. This surface quality inspection technique of the optical system would be a core metrological technology for production and supply of extreme-ultraviolet optical systems.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A point-diffraction interferometer for testing quality of an EUV (Extreme Ultraviolet) optical system like EUV lithography by use of a high-order harmonic X-ray, comprising:

a high power femtosecond laser;

a laser intensity controller for adjusting laser intensity and beam size of a femtosecond laser pulse generated by the high power femtosecond laser in order to reduce intensity of short wavelength harmonics with orders greater than a predetermined order;

a gas-filled hollow tube target for focusing the femtosecond laser beam in order to generate a high-order harmonic X-ray beam;

a gas pressure controller for adjusting the pressure of the target gas in order to reduce intensity of long wavelength harmonics with orders less than a predetermined order;

an interferometer plate implemented by a thin film having a pinhole and arranged to be perpendicular to an incident path of a high-order harmonic X-ray beam to generate a diffracted beam forming a reference and a transmitted beam; and an X-ray detector disposed on the path of the reference and transmitted beams to detect an interference pattern generated through the interference of the reference and transmitted beams.

2. The point-diffraction interferometer according to claim 1, wherein the interferometer plate is a thin foil in which pinholes are formed through a drilling technique using high power femtosecond laser.

3. The point-diffraction interferometer according to claim 1, wherein the high-order harmonic X-ray beam is generated so that a single harmonic order is dominantly generated by manipulating both the laser intensity controller and the gas pressure controller.

4. The point-diffraction interferometer according to claim 3, further comprising an X-ray filter disposed to be perpendicular to the path of the reference and transmitted beams between the interferometer plate and the X-ray detector to eliminate noise components originating from the femtosecond laser beam.

5. The point-diffraction interferometer according to claim 4, wherein the femtosecond laser pulse is generated so that a pulse width thereof is approximately 20 femtoseconds, and energy per pulse is approximately 0.35 mJ.

6. The point-diffraction interferometer according to claim 5, wherein the interferometer plate is movable along X and Y axes by actuators.

7. A high-order harmonic X-ray generation method for testing quality of an EUV (Extreme Ultraviolet) optical system like EUV lithography by use of the high-order harmonic X-ray, wherein the high-order harmonic X-ray is coherent and generated by focusing a high power femtosecond laser pulse generated by a high power femtosecond laser into a gas-filled hollow tube target, comprising the steps of:

reducing intensity of long-wavelength harmonics with orders less than a predetermined order by controlling the pressure of the target gas and using an X-ray filter with low transmissivity in a long wavelength region while the laser pulse is focused into the target;

reducing intensity of short wavelength harmonics with orders greater than the predetermined order by adjusting focused intensity of the high power femtosecond laser beam while the laser pulse is focused into the target; and allowing harmonics near the predetermined order to be phase-matched by adjusting the beam size of the high power femtosecond laser beam.

* * * * *